United States Patent
Chen et al.

(10) Patent No.: US 10,822,304 B2
(45) Date of Patent: Nov. 3, 2020

(54) PROCESS FOR THE PRODUCTION OF N-BOC-2-AMINO-3,3-DIMETHYLBUTYRIC ACID

(71) Applicant: Siegfried (Nantong) Pharmaceuticals Co. Ltd., Nantong Jiangsu (CN)

(72) Inventors: Jiang Chen, Haimen (CN); Christian Lothschuetz, Rheinfelden (DE); Beat Theodor Weber, Zofingen (CH)

(73) Assignee: Siegfried (Nantong) Pharmaceuticals Co. Ltd., Nantong Jiangsu (CN)

( * ) Notice: Subject to any disclaimer, the term of this patent is extended or adjusted under 35 U.S.C. 154(b) by 0 days.

(21) Appl. No.: 16/463,601

(22) PCT Filed: Nov. 23, 2017

(86) PCT No.: PCT/IB2017/057365
§ 371 (c)(1),
(2) Date: May 23, 2019

(87) PCT Pub. No.: WO2018/096484
PCT Pub. Date: May 31, 2018

(65) Prior Publication Data
US 2019/0276391 A1 Sep. 12, 2019

(30) Foreign Application Priority Data
Nov. 25, 2016 (CN) .......................... 2016 1 1056186

(51) Int. Cl.
C07C 269/04 (2006.01)
C07C 271/22 (2006.01)
C07C 271/12 (2006.01)

(52) U.S. Cl.
CPC .......... C07C 271/12 (2013.01); C07C 269/04 (2013.01)

(58) Field of Classification Search
CPC ............................ C07C 271/12; C07C 269/04
See application file for complete search history.

(56) References Cited

U.S. PATENT DOCUMENTS 3,855,238 A 12/1974 Batesky et al.
6,251,911 B1 6/2001 Bold et al.

FOREIGN PATENT DOCUMENTS

| CN | 102329376 A | 1/2012 | |
|---|---|---|---|
| CN | 103965299 | 8/2014 | |
| EP | 1 881 001 A1 | 1/2008 | |
| EP | 2 423 187 A1 | 2/2012 | |
| EP | 2423187 A1 * | 2/2012 | ........... C07C 269/04 |
| JP | 2003-146962 | 5/2003 | |
| JP | 2003146962 * | 5/2003 | |
| JP | 2004-175703 | 6/2004 | |
| JP | 2008-125364 | 6/2008 | |
| WO | WO 2011/069951 | 6/2011 | |

OTHER PUBLICATIONS

Cakici et al. (2011) Synthesis and asymmetric catalytic activity of (1S, 1'S)-4, 4'-biquinazoline-based primary amines. Tetrahedron: Asymmetry 22(3):300-308.
International Preliminary Report on Patentability for PCT/IB2017/057365 (dated May 28, 2019).
International Search Report for PCT/IB2017/057365 (dated Apr. 9, 2018).
Written Opinion of the ISA for PCT/IB2017/057365 (dated May 31, 2019).
Chinigo et al. (2008) Asymmetric synthesis of 2, 3-dihydro-2-arylquinazolin-4-ones: methodology and application to a potent fluorescent tubulin inhibitor with anticancer activity. Journal of Medicinal Chemistry 51(15) 4620-4631.
Liang et al. (Dec. 31, 2011) Synthesis study of tert-butoxycarbonyl-tert-leucine (Boc-tert-leucine) Pharmaceutical and Clinical Research 19(3):282-283.
Office Action corresponding to Chinese Patent Application No. 201611056186.8 dated Dec. 18, 2019.
Supplementary European Search Report and Opinion for EP Patent Application 17873568.4 dated Jan. 28, 2020.

* cited by examiner

Primary Examiner — Paul A Zucker
(74) Attorney, Agent, or Firm — Jenkins, Wilson, Taylor & Hunt, P.A.

(57) ABSTRACT

The current invention offers a process for the production of N-Boc-2-amino-3,3-dimethylbutyric acid by a reaction of tert-Leucine with di-tert-butyl-dicarbonate, the process comprising (i) contacting the tert-Leucine with di-tert-butyl-dicarbonate in an aqueous medium, optionally comprising a first organic solvent, in the presence of an inorganic base, (ii) optionally removing the first organic solvent, (iii) optionally extracting the resulting N-Boc-2-amino-3,3-dimethylbutyric acid into a second organic solvent, (iv) isolating the product by precipitation from the reaction mixture at acidic pH, and (v) optionally reuse the first and/or second organic solvents recovered from step (ii) and/or step (iv) for the next production cycle. The process is sufficiently short, uses preferably environmental friendly solvents, avoids waste and leads to good yields.

14 Claims, No Drawings

PROCESS FOR THE PRODUCTION OF N-BOC-2-AMINO-3,3-DIMETHYLBUTYRIC ACID

FIELD OF THE INVENTION

The present invention relates to a novel method of manufacturing N-Boc-2-amino-3,3-dimethylbutyric acid, also called N-Boc-tert-Leucine. The method is characterized in that it offers a direct and environmental friendly process with limited, recyclable use of organic solvent, and at the same time leads to good yield and high purity. The compound N-Boc-2-amino-3,3-dimethylbutyric acid is one of the key intermediates to prepare various substances used as agrochemicals or as active pharmaceutical ingredients, for example, but not limited to, as protease inhibitors for the treatment of hepatitis C. Further, N-Boc-2-amino-3,3-dimethylbutyric acid is also useful for the synthesis of drugs like Asunaprevir, Boceprevir, Telaprevir, Taltobulin, Verdroprevir, and several other drugs being marketed or being in early development stages or clinical phases. Recently, also the use as phase-transfer catalyst has been reported.

STATE OF THE ART

N-Boc-tert-Leucine is one of the key intermediates to prepare various substances used as agrochemicals or as active pharmaceutical ingredients. N-tert-butoxycarbonyl amino acids have been prepared for several years.

Published processes for the production of N-Boc-tert-Leucine couple tert-Leucine with Boc anhydride (di-tert-butyl-dicarbonate) in the presence of a base. Published processes use either organic amine bases, which eventually have to be disposed or recycled in tedious operations. A second process is the use of inorganic bases in combination with downstream extraction of the product into an organic phase, a time consuming and resource intense procedure.

JP 2004-175703 discloses a production process of an N-alcoxycarbonyl-tert-Leucine using an excessive N-alcoxycarbonylating agent with maintaining the pH between 11 and 13.

JP 2001-501216 describes a production process of an N-alcoxycarbonyl-tert-Leucine by adding an excessive amount of sodium hydroxide in advance to obtain a strongly basic aqueous solution of tert-Leucine and then adding an equimolar amount of an N-alcoxycarbonylating agent to the solution.

JP 2003-146962 and JP 2008-125364 disclose a process for production of an N-tert-butoxy-carbonyl-L-tert-Leucine by mixing di-tert-butyl dicarbonate with L-tert-Leucine.

U.S. Pat. No. 3,855,238 describes a generic process of reacting a base addition salt of an amino acid with O-tert-butyl S-phenyl thiocarbonate in dimethyl sulfoxide as solvent to form a desired N-tert-butoxycarbonyl amino acid. N-Boc-2-amino-3,3-dimethylbutyric acid has been prepared with an yield of 65%. In another example the use of methanol as solvent and benzyltrimethylammonium hydroxide (Triton B) as based resulted in a yield of 60%.

EP 1 881 001 discloses an example wherein, to a solution of L-tert-Leucine and di-tert-butyl dicarbonate (1.0:1.2) in a mixture of dioxane and water (1:1), an organic base (trimethylamine, 5 to 6 times in excess) is added. After extraction and purification N-Boc-L-tert-Leucine was obtained with 58% yield.

WO 2011/069951 discloses a preparation of N-protected amino acids from amino acids with Boc anhydride in the presence of a base in an organic solvent such as THF (tetrahydrofuran), methanol, dioxane, or dichloromethane.

Further examples for N-alkoxylation and the required purification process can be found in Cakici et al., Tetrahedron: Asymmetry 22 (3), 2011, p 300-308.

Even though the synthesis disclosed in literature is straightforward, there is a demand for improvement.

SUMMARY OF THE INVENTION

The current invention offers a novel method for manufacturing N-Boc-2-amino-3,3-dimethylbutyric acid (N-Boc-tert-Leucine) in a short process, using environmental friendly solvents, avoiding waste or offering a recycle process, and leading to a pure product at good yields.

The present invention relates to a method for preparing (a) N-Boc-L-tert-Leucine (1a) from L-tert-Leucine (2a) as disclosed in scheme 1, (b) N-Boc-D-tert-Leucine (1b) from D-tert-Leucine (2b) as disclosed in scheme 2, or all possible mixtures of the two offered options (a) and (b).

Scheme 1

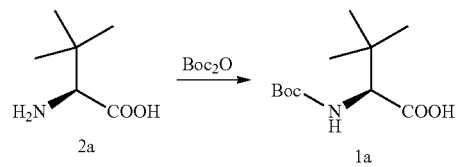

Scheme 2

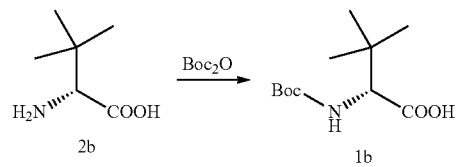

This invention presents a process, which uses an inorganic base and eliminates the need to extract the product into an organic solvent. Therefore, the process is easier to execute since the number of unit operations is limited and the process is ecologically friendlier due to the limited use of organic solvents.

DETAILED DESCRIPTION OF THE INVENTION

All ranges disclosed herein are to be considered to be supplemented by the term "about", unless clearly defined to the contrary or otherwise clear from the context.

The current invention offers a novel method for manufacturing N-Boc-2-amino-3,3-dimethylbutyric acid (N-Boc-tert-Leucine) in an efficient reaction as disclosed in detail below.

The invention relates to a process for the production of N-Boc-2-amino-3,3-dimethylbutyric acid by a reaction of tert-Leucine with di-tert-butyl-dicarbonate, the process comprising (i) contacting the tert-Leucine with di-tert-butyl-dicarbonate in an aqueous medium, optionally comprising a first organic solvent, in the presence of an inorganic base, (ii) optionally removing the first organic solvent, (iii) optionally extracting the resulting N-Boc-2-amino-3,3-dimethylbutyric acid with a second organic solvent, (iv) isolating the product by precipitation from the reaction mixture at acidic pH, and (v) optionally reuse the first and/or second organic solvents recovered from step (ii) and/or step (iv) for a next production cycle. According to certain embodiments the different steps are carried out in this order, e.g. with steps (i), (ii), (iii), (iv) and (v); steps (i), (ii), (iii), (iv); steps (i), (ii), (iv) and (v); steps (i), (ii) and (iv); steps (i), (iv) and (v); steps (i) and (iv); steps (i), (iii), (iv) and (v); or steps (i), (iii) and (iv).

In a first step the process comprises (i) contacting the tert-Leucine with di-tert-butyl-dicarbonate in an aqueous medium, optionally comprising a first organic solvent, in the presence of an inorganic base.

The process following the current invention uses an aqueous solvent system containing at least 50% by weight water, particularly in step (i). However, also a first organic solvent can be present in step (i), which is not particularly restricted, with at most 50% by weight, based on the total weight of solvent in step (i). A boiling point of the first organic solvent, if present, is preferably below 200° C.

In one aspect of the invention the first and/or second organic solvent used can be one single solvent, or can be a mixture of different solvents. Preferably the first and/or second organic solvent is selected from the group of alcohols, ketones, alkyl carbonates, nitriles and ethers; more preferably from alcohols, alkyl carbonates, ketones and ethers; further more preferably from alcohols, alkyl carbonates and ketones. The first and/or second organic solvent may be used as single compound or as mixture composed of said organic solvents. For the organic solvents, an alkyl residue can be linear or branched and can comprise a suitable number of carbon atoms for a solvent, e.g. from 1 to 20 carbon atoms. Further, alkyl carbonates cover salts of carbonic acid, e.g. also esters.

In one aspect of the invention the first organic solvent used can be one single solvent, or can be a mixture of different solvents. Preferably the first organic solvent is selected from the group of alcohols, ketones, alkyl carbonates, nitriles and ethers; more preferably from alcohols, alkyl carbonates, ketones and ethers; further more preferably from alcohols, alkyl carbonates and ketones. The first organic solvent may be used as single compound or as mixture composed of said organic solvents. Suitable first organic solvents include e.g. ketones like acetone, ethers like THF, carbonates like diethylcarbonate, and/or alcohols like tert-butyl alcohol.

In one aspect of the invention the first and/or second, e.g. first, organic solvent is tert-butanol, which can be liberated during the manufacturing process. Tert-butanol can be used as exclusive first and/or second, e.g. first, organic solvent or in combinations with one or more other solvents which can be miscible with water or which may not be miscible with water, e.g. in step (i).

In one aspect of the invention the first and/or second, preferably at least the first, organic solvent is volatile, i.e. has a boiling point below 200° C. at normal pressure of 101 325 Pa, and therefore can be removed by distillation, for example. According to certain embodiments, the first organic solvent is volatile and has a boiling point below 150° C., preferably below 100° C. at normal pressure and/or ambient pressure. The organic, volatile solvent, e.g. first and/or second organic solvent, may be removed from the reaction mixture and can be directly reused in subsequent batches. Particularly, the recovered solvent, particularly first and/or second organic solvent, can be of high purity and be reused in a subsequent batch without any loss without any further processing.

In step (i) the first organic solvent, if present, can be a water miscible organic solvent or an organic solvent that is not fully miscible with water. However, the solvent used to extract non-desired side products is "not fully" or not miscible with water, i.e. forming two phases.

In one aspect of the invention a first and/or second, particularly second, organic solvent is selected which is not fully miscible with water. In this regard an organic solvent that is not fully miscible with water particularly is an organic solvent that will separate from water upon shaking, i.e. forms two separate phases. Inventors found the reaction to take course without any restriction. This type of inventive process allows a direct phase split without removing the organic solvent from the reaction. More preferably this process even allows a phase split without addition of a second solvent, e.g. a second organic solvent for extraction. Examples of such organic solvents, particularly first organic solvents that are not fully miscible with water include e.g. apolar organic solvents, like diethyl carbonate, tert-butanol, methyl-tetrahydrofurane, toluene, benzene, hexane, chloroform, dichloromethane or carbon tetrachloride. According to certain embodiments the first organic solvent is a solvent which allows a, e.g. spontaneous, phase separation after completion of the reaction in step (i) without adding a further solvent.

The reagents tert-Leucine and Boc anhydride are coupled in the presence of an inorganic base, which is not particularly restricted as long as it is inorganic and a base, i.e. can form $OH^-$ ions in water and is not organic. The inorganic base may be preferably selected from any accessible, water soluble base. Preferable examples of the inorganic base are NaOH and KOH.

In one aspect of the invention any inorganic base can be used, as well as mixtures thereof. Preferably the inorganic base is selected from any base having a cationic counterion/cation selected from cations of the alkali metal and/or earth-alkali metal group of the periodic table. Preferably the cation of the inorganic base is selected from cations of the alkali metal group, and more preferably either cations of sodium and/or potassium are used as cation. Such bases may either be the hydroxyl compounds of said metal cations or alkaline salts thereof like, but not limited to, carbonates or bicarbonates. Suitable examples of inorganic bases include e.g. sodium hydroxide, sodium carbonate, sodium bicarbonate, potassium hydroxide, potassium carbonate, potassium bicarbonate, magnesium hydroxide, magnesium carbonate, magnesium bicarbonate, calcium hydroxide, calcium carbonate, calcium bicarbonate, or mixtures thereof, which can be applied e.g. as such or in a suitable solvent, e.g. in water.

The reaction according to step (i) may be preferably executed at a temperature at which the selected solvent system is liquid. Preferably the reaction is executed at a temperature in a range between 0° C. and 100° C., e.g. between 10° C. and 80° C., preferably between 20° C. and 50° C. According to certain embodiments the reaction temperature in step (i) is kept below 50° C., which can be e.g. achieved by sufficient cooling and/or by sufficiently slow addition of reagents.

In one aspect of the invention the process is executed at a temperature where the solvents and the solvent system is liquid. Preferably a temperature is chosen such that the reaction is completed up to 99% in less than 10 hours. Inventors found that most solvents and solvent systems work well in temperature range between 20° C. and 50° C.

After step (i) an optional step (ii) of removing the first organic solvent may take place, which can depend on the type of first organic solvent used and if it interferes in the isolating step (iv) or not. The type of removing thereby is not particularly restricted and can be e.g. carried out by decanting, e.g. if a phase split is present, distillation, evaporation, etc. The removed first organic solvent may be reused in the present process.

The remainder may be extracted in an optional step (iii) with, preferably a small volume of, a second organic solvent, preferably not miscible with water, to remove possible by-products. Remainder traces of solvents and possible side-products can thus in addition or alternatively be extracted with a small volume of a second organic solvent that is preferably not miscible with water. This means that in step (iii) side products can be extracted into the second organic solvent.

The product of the present reaction, i.e. N-Boc-2-amino-3,3-dimethylbutyric acid, can stay in the aqueous phase.

The second organic solvent is not particularly restricted and can be different from the first organic solvent or identical to the first organic solvent, but is preferably different to the first organic solvent. Preferably the second organic solvent is selected from the group of alcohols, ketones, alkyl carbonates, nitriles and ethers; more preferably from alcohols, alkyl carbonates, ketones and ethers; further more preferably from alcohols, alkyl carbonates and ketones. The second organic solvent may be used as single compound or as mixture composed of said organic solvents. Suitable second organic solvents include e.g. alcohols, e.g. aromatic alcohols, like toluene, and/or carbonates, e.g. esters, like ethyl acetate, but the second organic solvent is not limited thereto. Preferably the second organic solvent is not fully miscible or not miscible with water.

According to certain embodiments, the second organic solvent is comprised with less than 1 volume unit, particularly with regard to the remaining solvent after step (i) or after step (ii)—i.e. the aqueous medium optionally comprising the first organic solvent if step (ii) is not carried out, and/or essentially the aqueous medium, e.g. water, if step (ii) is carried out or if the first organic solvent is not contained, further particularly with regard to the amount of water used in step (i), preferably with less than 0.5 volume units, further preferably with 0.2 volume units or less.

The extraction itself is not particularly limited, and the second organic solvent can be mixed with the water of step (i) and optionally a first organic solvent e.g. by shaking, pressure injection, etc.

Preferably the extraction with an organic solvent in step (iii) takes place at a pH value of more than 7, e.g. more than 8, e.g. at a pH above 9. According to certain embodiments the pH is kept below 13, e.g. below 12.

The product N-Boc-tert-Leucine is precipitated in step (iv) by acidifying, e.g. the aqueous phase, and isolation can take place by filtration, for example. The acidifying is not particularly restricted and can be done by adding a suitable acid, preferably an acid that can achieve a sufficiently low pH in water. Suitable acids can be organic and/or inorganic, and also mixtures of acids can be added. The acids can be added as such or in form of a solution in a suitable solvent, e.g. water. Suitable acids include, but are not limited to e.g. HCl, HBr, HI, $H_2SO_4$.$H_3PO_4$, $H_3PO_3$, citric acid, malonic acid, formic acid, acetic acid, or mixtures thereof, particularly HCl and/or $H_2SO_4$. In step (iv) the pH value is preferably adjusted in the range of 1 to 5 and/or temperature is kept below 50° C., and more preferably pH is adjusted into the range of 2 to 4 and/or temperature is kept below 30° C.

As stated the acid can be added in a solvent that is not particularly restricted, so that the solvent can be e.g. water or a third organic solvent, or mixtures thereof, which are not particularly restricted. If a third organic solvent is added it is preferred that it is not miscible with water, e.g. like the second organic solvent. However, it is preferred that water is used as a solvent for the acid if a solvent is used. If a third organic solvent is used it can also be removed and optionally reused in the present process.

Furthermore, also the isolation is not particularly restricted, and apart from filtration other separation steps can be used, e.g. centrifugation, decantation, evaporation, etc.

In a further aspect of the invention the remaining inorganic phase is subsequently treated with an acid to precipitate and/or to crystallize the product N-Boc-tert-Leucine. This step allows easy isolation of the desired end product, e.g. by solid liquid separation, as for example by filtration. It has been found that preferably pH value is kept in the range of 1 to 5 and/or temperature is kept below 50° C.; more preferably pH is adjusted into the range of 2 to 4 and/or temperature is kept below 30° C. The acid for pH adjustment may either be selected from inorganic or organic acids. Preferably the acid selected should form a salt which remains dissolved in the available amount of water. Acids well suited for said purpose are selected for the group of hydrochloric acid, sulfuric acid, acetic acid, formic acid and citric acid.

In the isolation step (iv) it is also possible to add seed crystals of N-Boc-2-amino-3,3-dimethylbutyric acid to facilitate precipitation of the product. The amount of seed crystals thereby is not particularly restricted.

Further, the optional step (v) of reusing the first and/or second organic solvents that are recovered is not particularly restricted, and this also can include a purification of the solvent prior to the reuse, e.g. if side products or impurities of the reaction are contained. In addition, also water and/or an optional third organic solvent can be reused in the same way.

In one aspect of the invention the process offers the manufactured end product N-Boc-2-amino-3,3-dimethylbutyric acid (N-Boc-tert-Leucine) in a purity of more than 98.0 area-% as measured by HPLC (standard High Performance Liquid Chromatography procedure) without any further purification step. In various trials purity levels of at least 99.0 area-%, and in most trials purity levels of 99.5 area-% or above and even above 99.8 area-% have been detected.

In one aspect of the invention conversion rates from tert-Leucine and Boc anhydride to N-Boc-tert-Leucine equal or above 99.0% can be reached using this novel process.

The disclosed novel process is not limited to any form of tert-leucine. Furthermore the process can be used to produce N-Boc-L-tert-Leucine from L-tert-Leucine, N-Boc-D-tert-Leucine from D-tert-Leucine, or any mixture of N-Boc-L-tert-Leucine and N-Boc-D-tert-Leucine, including the racemic 1:1 mixture.

EXAMPLES

The present invention will now be described in detail with reference to several examples thereof. However, these examples are illustrative and do not limit the scope of the invention.

Example 1

In a mixture of 50 ml water and acetone (ratio 2:1 by weight) 10 g tert-Leucine, 8 g sodium carbonate and 20 g Boc anhydride are charged. The mixture is stirred at room temperature, e.g. of about 25 to about 30° C., until the conversion is >99% (takes about 3 hours). The pH is kept above 9, and, if needed, sodium carbonate is added. The acetone is removed by vacuum distillation, and the distillate can be reused in a subsequent batch. The remainder is extracted with 5 ml toluene. The organic phase is distilled, and the toluene fraction can be reused in the subsequent batch. The inorganic phase is acidified to pH 2 to 4 by addition of hydrochloric acid, and 0.1 g of seed crystals are added. The precipitated product is isolated by filtration, washed with water and dried at 40° C. under vacuum. Yield is 16.8 g, equal to 94% N-Boc-tert-Leucine. HPLC analysis shows a purity of 99.89 area-%.

Example 2

In a mixture of 50 ml water and acetone (ratio 1:1 by weight) 10 g tert-Leucine, 4 g sodium carbonate and 10 g Boc anhydride are charged. The mixture is stirred at room temperature until the conversion is >99% (takes about 5 hours). The pH is kept above 9 but below 12. If needed, potassium hydroxide is added to adjust the pH value of the mixture. The acetone is removed by vacuum distillation, and the remainder is extracted with 5 ml toluene. The acetone distilled from the reaction mixture and from the toluene extract is united and can be directly reused in the next batch. Toluene can be reused directly in the next batch too. The inorganic phase is acidified to pH 3 to 4 by addition of citric acid, and 0.1 g of seed crystals are added. The precipitated product is isolated by filtration, washed with water and dried at 40° C. under vacuum. Yield is 16.3 g, equal to 91% N-Boc-tert-Leucine. HPLC analysis shows a purity of 99.90 area-%.

Example 3

In a mixture of 90 ml water and acetone (ratio 1:1 by weight) 10 g tert-Leucine, 8 g calcium hydroxide and 20 g Boc anhydride are charged. The mixture is stirred at room temperature until the conversion is >99%. The acetone is removed by vacuum distillation, and the remainder is extracted with 9 ml ethyl acetate. The acetone distilled from the reaction mixture and from the ethyl acetate extract is united and can be directly reused in the next batch. Ethyl acetate can be reused in the next batch too. The inorganic phase is acidified to pH 2 to 4 until all solids are dissolved by addition of hydrochloric acid. The precipitated product is isolated by filtration, washed with water and dried at 40° C. under vacuum. Yield is 17.2 g, equal to 96% N-Boc-tert-Leucine. HPLC analysis shows a purity of 99.8 area-%.

Example 4

In a mixture of 70 ml water and tetrahydrofuran (ratio 3:2 by weight) 10 g tert-Leucine, 11 g potassium carbonate and 19 g Boc anhydride are charged. The mixture is stirred at room temperature until the conversion is >99% (takes about 5 hours). The tetrahydrofuran is removed by vacuum distillation, and the remainder is extracted with 5 ml toluene. The tetrahydrofuran distilled from the reaction mixture can be directly reused in the next batch. The inorganic phase is acidified to pH 3 to 4 by addition of citric acid, and 0.1 g of seed crystals are added. The precipitated product is isolated by filtration, washed with water and dried at 40° C. under vacuum. Yield is 16.3 g, equal to 91% N-Boc-tert-Leucine. HPLC analysis shows a purity of 99.2 area-%.

Example 5

In a mixture of 40 ml water and diethyl carbonate (ratio 5:1 by weight) 10 g tert-Leucine, 8 g sodium carbonate and 19 g Boc anhydride are charged. The mixture is stirred at room temperature until the conversion is >99% (takes about 5 hours). pH is kept above 9, and, if needed, sodium carbonate is added to adjust the pH value of the mixture. Stirring is stopped and the upper organic layer is removed. The inorganic phase is acidified to pH 2 to 4 by addition of hydrochloric acid, and 0.1 g of seed crystals are added. The precipitated product is isolated by filtration, washed with water and vacuum dried at 40° C. Yield is 16.8 g, equal to 94% N-Boc-tert-Leucine. HPLC analysis shows a purity of 99.7 area-%.

Example 6

In 50 ml water 10.0 g tert-leucine, 8 g sodium carbonate and 20 g Boc anhydride are charged. The mixture is stirred at 30° C. until the conversion is >99% (takes about 3 hours). pH is kept above 9, and, if needed, sodium carbonate is added. Then 5 ml toluene is used to extract neutral organic by-products. The organic phase is separated by distillation, and the toluene fraction can be directly used in subsequent batches. The inorganic phase is acidified at room temperature to pH 2 to 4 by addition of hydrochloric acid, and 0.1 g of seed crystals are added. The precipitated product is isolated by filtration, washed with water and dried at 40° C. under vacuum. Yield is 15.9 g, equal to 90% N-Boc-tert-leucine. HPLC analysis shows a purity of 99.6 area-%.

Example 7

In a mixture of 50 ml water and acetone (ratio 2:1 by weight) 10.0 g tert-leucine, 8 g sodium carbonate and 20 g Boc anhydride are charged. The mixture is stirred at room temperature until the conversion is >99% (takes about 3 hours). pH is kept above 9, and, if needed, sodium carbonate is added. The inorganic phase is acidified to pH 2 to 4 by addition of hydrochloric acid, and 0.1 g of seed crystals are added. The precipitated product is isolated by filtration, washed with water and dried at 40° C. under vacuum. Yield is 12.9 g, equal to 73% of N-Boc-tert-leucine. HPLC analysis shows a purity of 99.9 area-%.

Example 8

In a mixture of 50 ml water and tert-butanol (ratio 4:1 by weight) 10.0 g tert-leucine, 8 g sodium carbonate and 20 g Boc anhydride are charged. The mixture is stirred at room temperature until the conversion is >99% (takes about 4 hours). pH is kept above 9, and, if needed, sodium carbonate is added. Stirring is stopped and the upper organic layer is removed. The inorganic phase is acidified to pH 2 to 4 by addition of hydrochloric acid, and 0.1 g of seed crystals are added. The precipitated product is isolated by filtration, washed with water and dried at 40° C. under vacuum. Yield is 14.6 g, equal to 83% of N-Boc-tert-leucine. HPLC analysis shows a purity of 99 area-%.

The invention claimed is:
1. A process for the production of N-Boc-2-amino-3,3-dimethylbutyric acid by a reaction of tert-Leucine with di-tert-butyl-dicarbonate, the process comprising (i) contact- ing the tert-Leucine with di-tert-butyl-dicarbonate in an aqueous medium comprising tert-butanol as a first organic solvent in the presence of an inorganic base, (ii) optionally removing the first organic solvent, (iii) optionally extracting the resulting N-Boc-2-amino-3,3-dimethylbutyric acid with a second organic solvent, (iv) isolating the product by precipitation from the reaction mixture at pH 2-4, and (v) optionally reusing the first and/or second organic solvents recovered from step (ii) and/or step (iv) for a next production cycle.

2. The process according to claim 1 wherein the tert-leucine is L-tert-Leucine.

3. The process according to claim 1 wherein the tert-leucine is D-tert-Leucine.

4. The process according to claim 1 wherein as tert-leucine a mixture of L-tert-Leucine and D-tert-Leucine is used.

5. The process according to claim 1 wherein extraction with an organic solvent in step (iii) takes place at pH value >7.

6. The process according to claim 1 wherein extracting step (iii) is carried out with the second organic solvent present in an amount of less than 1 volume as compared to the volume of the solution extracted.

7. The process according to claim 1 wherein the tert-butanol is removed in step (ii) prior to extraction.

8. The process according to claim 1 wherein the aqueous medium in step (i) contains a water miscible organic solvent.

9. The process according to claim 1 wherein the ratio of the tert-butanol is less than 50% of the total solvent volume in step (i).

10. The process according to claim 1 wherein the tert-butanol allows a spontaneous phase separation after completion of the reaction in step (i) without adding a further solvent.

11. The process according to claim 1 wherein the reaction temperature in step (i) is kept below 50° C.

12. The process according to claim 1 wherein the temperature when adjusting the pH value and isolation of the product in step (iv) is below 30° C.

13. The process according to claim 1 wherein the base in step (i) comprises a cation selected from cations of alkali metals or alkaline earth metals.

14. The process according to claim 1 wherein the molar ratio of Boc anhydride to tert-leucine is from 1.1:1 to 1.2:1.

* * * * *